United States Patent
Högerle et al.

(10) Patent No.: US 12,036,048 B2
(45) Date of Patent: Jul. 16, 2024

(54) HOLDING APPARATUS AND PRODUCT MONITORING SYSTEM

(71) Applicant: Aesculap AG, Tuttlingen (DE)

(72) Inventors: Roland-Alois Högerle, Tuttlingen (DE); Stephanie Auber, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 241 days.

(21) Appl. No.: 17/289,308

(22) PCT Filed: Oct. 28, 2019

(86) PCT No.: PCT/EP2019/079342
§ 371 (c)(1),
(2) Date: Apr. 28, 2021

(87) PCT Pub. No.: WO2020/089142
PCT Pub. Date: May 7, 2020

(65) Prior Publication Data
US 2022/0008155 A1    Jan. 13, 2022

(30) Foreign Application Priority Data
Oct. 29, 2018    (DE) .................... 10 2018 126 969.2

(51) Int. Cl.
*A61B 50/20*    (2016.01)
*A61B 90/70*    (2016.01)
(Continued)

(52) U.S. Cl.
CPC .............. *A61B 50/20* (2016.02); *A61B 90/70* (2016.02); *A61L 2/18* (2013.01); *A61L 2/28* (2013.01);
(Continued)

(58) Field of Classification Search
CPC ..... A61B 1/125; A61B 1/00144; A61B 50/20; A61B 90/70; A61L 2/18; A61L 2/28; A61L 2202/17; A61L 2202/24; A61C 19/002
See application file for complete search history.

(56) References Cited

U.S. PATENT DOCUMENTS 5,380,369 A * 1/1995 Steinhauser ......... A61C 19/002
134/1
9,101,337 B2   8/2015 Hoegerle et al.
(Continued)

FOREIGN PATENT DOCUMENTS

DE    102009051619 A1    5/2011
DE    102010017624 A1    12/2011
(Continued)

OTHER PUBLICATIONS

TPC Advanced Technology, "H6000, 6005, & 6025 Handpiece Cleaning and Lubrication System User Manual", available online Jun. 22, 2012 (Year: 2012).*
(Continued)

*Primary Examiner* — Jennifer Wecker
*Assistant Examiner* — Brady C Pilsbury
(74) *Attorney, Agent, or Firm* — Christopher A. Rothe; Culhane PLLC

(57) ABSTRACT

A holding apparatus for holding a sterilizable medical product and for storing the medical product before and/or after the cleaning process, and a product monitoring system featuring such a holding apparatus. The holding apparatus includes a data processing device connectable to at least one sensor in a signal-conducting manner. The sensor is a temperature sensor for determining a temperature during the cleaning process and/or a pressure sensor for determining a static and/or dynamic pressure of a cleaning fluid during the cleaning process. The data processing device processes the
(Continued)

sensor signals to form cleaning information and is connectable to a memory apparatus in a data-conducting manner, on which memory apparatus the cleaning information is storable. The cleaning information is retrievable or readable from the memory apparatus by an evaluation device such that a cleaning profile of the medical product can be determined based on the cleaning information.

24 Claims, 3 Drawing Sheets

(51) Int. Cl.
    *A61L 2/18*     (2006.01)
    *A61L 2/28*     (2006.01)

(52) U.S. Cl.
    CPC ....... *A61L 2202/17* (2013.01); *A61L 2202/24* (2013.01)

(56) References Cited

U.S. PATENT DOCUMENTS

| | | | |
|---|---|---|---|
| 10,368,958 B2 | 8/2019 | Wehrle et al. | |
| 2004/0209223 A1* | 10/2004 | Beier | A61C 19/002 433/126 |
| 2008/0130706 A1 | 6/2008 | Kellner et al. | |
| 2009/0128330 A1* | 5/2009 | Monroe | G16H 20/17 340/568.1 |
| 2009/0261549 A1 | 10/2009 | Kral | |
| 2017/0277864 A1* | 9/2017 | Bassion, Sr. | A61B 90/70 |
| 2018/0052454 A1* | 2/2018 | Magno | A61C 19/002 |
| 2018/0228341 A1* | 8/2018 | Stojalowski | A61L 2/18 |
| 2018/0353275 A1* | 12/2018 | St. Louis | A61C 1/0007 |

FOREIGN PATENT DOCUMENTS

| | | | |
|---|---|---|---|
| DE | 102011050192 A1 | 11/2012 | |
| DE | 102015108264 A1 | 12/2016 | |
| EP | 2514386 A1 | 10/2012 | |
| JP | 2009136492 A | 6/2009 | |
| JP | 2009172013 A | 8/2009 | |
| JP | 2017205358 A | 11/2017 | |
| KR | 1909009 B1 * | 10/2018 | A61C 1/12 |
| WO | 03092524 A1 | 11/2003 | |
| WO | 2008020770 A1 | 2/2008 | |

OTHER PUBLICATIONS

International Search Report received in Application No. PCT/EP2019/079342 dated Feb. 13, 2020, with translation, 7 pages.
Search Report received in German Application No. 10 2018 126 969.2 dated Aug. 20, 2019, with translation, 20 pages.
Written Opinion received in International Application No. PCT/EP2019/079342 dated Feb. 13, 2020, with translation, 11 pages.
Office Action received in Japanese Application No. 2021-523082 dated Jun. 14, 2023, with translation, 22 pages.
Office Action received in Chinese Application No. 201980069835.3 dated Sep. 28, 2023, with translation, 13 pages.

* cited by examiner

HOLDING APPARATUS AND PRODUCT MONITORING SYSTEM

CROSS-REFERENCE TO RELATED APPLICATION(S)

This application is the United States national phase entry of International Application No. PCT/EP2019/079342, filed Oct. 28, 2019, and claims the benefit of priority of German Application No. 10 2018 126 969.2, filed Oct. 29, 2018. The contents of International Application No. PCT/EP2019/079342 and German Application No. 10 2018 126 969.2 are incorporated by reference herein in their entireties.

FIELD

The present invention relates to a holding apparatus for holding at least one sterilizable medical product, in particular during a cleaning process, as well as for storing the medical product before and/or after the cleaning process.

BACKGROUND

Holding apparatuses of the present type are provided, among other things, for cleaning and holding motors and handpieces of surgical instruments and are described, inter alia, in DE 10 2010 017 624. The holders are arranged with medical products arranged in the holders in medical cleaning systems, in particular sterilizers, rinsing systems or the like. In addition, it is also possible for the holders to be used together with sterile containers and to be arranged within them, so that after sterilization of the medical products it is ensured that renewed contamination of the medical products is effectively prevented.

It is also common practice, for example, for reusable implants to be reprocessed in a way similar to the surgical instruments mentioned. For a large number of these reprocessable implants, in particular if they are made of titanium, frequent reprocessing leads to losses in the quality of the medical product. In the case of titanium screws, for example, the thickness of the oxide layer protecting the titanium screw from corrosion and biofilm formation is reduced by the frequent use of aggressive cleaning substances. Reprocessable implants often come in sets which, regardless of whether individual elements of the set are actually used, always undergo a reprocessing process together.

From the prior art, for example according to relevant products of the present applicant, holders of the type described above are known which accompany the medical products held therein throughout the entire cleaning and reprocessing process. Such a holder is known, for example, from DE 10 2010 017 624.

In order to be able to track how often a medical product has been reprocessed during its service life, it is known, for example, to provide integrated temperature sensors with independent energy supply units or energy harvesting units in a motor of the medical product, which record the temperature during the cleaning process and store it in a data memory of the motor. A motor with storage devices suitable for this purpose is described, for example, in DE 10 2011 050 192. In particular, the disadvantage here is that such a solution takes up a relatively large installation space in the medical product and increases its weight. In particular, these disadvantages are not acceptable for medical products for use in the field of neurosurgery, minimally invasive procedures, or the like.

It has been shown to be important in the monitoring of medical products that
a change in the volume and/or weight of the medical product itself is avoided as far as possible, and
monitoring of individual medical products is possible.
Furthermore, it would be desirable that
the recorded data can be read out wirelessly,
the recorded data can be supplied for evaluation, and
that the data can be accessed worldwide.

SUMMARY

In view of the preceding description of the prior art, it is the object of the present invention to provide a holding apparatus for sterilizable medical products by means of which the aforementioned desirable properties can be achieved as far as possible in their entirety.

Accordingly, the present invention relates to a holding apparatus for holding at least one sterilizable medical product, in particular during a cleaning process, and for storing the medical product before and/or after the cleaning process. According to the invention, the holding apparatus has a data processing device which is/can be connected to at least one sensor in a signal-conducting manner, wherein the sensor is in particular a temperature sensor for determining a temperature during the cleaning process and/or a pressure sensor for determining a static and/or dynamic pressure of a cleaning fluid during the cleaning process. The data processing device processes the sensor signals to become cleaning information and has a storage device and/or is/can be connected in a data-conducting manner to a storage device on which the cleaning information is/can be stored. The cleaning information can be retrieved/read out from the storage device by an evaluation device, so that a cleaning profile of the medical product can be determined by the evaluation device on the basis of the cleaning information.

Accordingly, it is possible to document the cleaning process of the medical product by means of the cleaning profile without changing the volume and/or the weight of the medical product. In particular, it is also provided that courses of the sensor data are to be part of the cleaning profile. The signal-conducting connection between the data processing device and the sensor can be established, for example, by means of a cable connection and/or a wireless connection. In addition to determining the pressure of the cleaning agent and the temperature, it is also provided that, for example, an amount of cleaning oil, a pH value, a conductivity or the like can be determined by means of one or more sensors. It is provided that for all determined data also courses, cycles, dwell times, time courses or the like can be recorded.

It is provided that the data processing device can also be a so-called SOC (System On a Chip), for example. In order to be able to use the data processing device on the holder, i.e. inside/within an area to be cleaned and/or sterilized, it is provided that the data processing device is protected against environmental influences.

The evaluation device may be, for example, a PC, a laptop, a tablet or the like. Furthermore, it is also possible that the evaluation device can be designed as a component of a further computer system, for example a control device of the medical product.

In an advantageous embodiment of the invention, it is provided that the holding apparatus has a supply line and at least one cleaning line branching off from the supply line, to which a rinsing receptacle for receiving the medical product, in particular a handpiece, is connected, wherein the cleaning agent can be supplied through the supply line, the cleaning line and the rinsing receptacle into sections to be cleaned, in particular of the handpiece. Handpieces in the sense of the invention means the handpieces of surgical instruments described above.

It is also advantageously provided that the holding apparatus can have a plurality of cleaning lines, wherein each cleaning line is associated with a rinsing receptacle, so that it is possible to determine by monitoring the cleaning line whether a cleaning process has been carried out in accordance with predetermined parameters and whether the medical products, in particular handpieces, arranged on the rinsing receptacles have been adequately cleaned.

An advantageous embodiment of the invention provides that a temperature sensor and/or a pressure sensor is/are arranged in the supply line and/or the cleaning line and/or the rinsing receptacle. Due to a thermodynamic and hydraulic coupling between the supply line, the cleaning lines and the rinsing receptacle, it is sufficient for determining the cleaning profile when each cleaning line has a pressure sensor and the supply line has a temperature sensor.

The determined temperature in the supply line and the pressure in the cleaning lines during the cleaning process define the parameters by means of which it can be determined that the cleaning process of each medical product, in particular a handpiece, has been passed in a form that guarantees proper and hygienic reprocessing.

In order to achieve a simple structure of the holding apparatus, it is also possible and provided that only the supply line can have both a pressure sensor and a temperature sensor. This is in particular advantageous if mainly similar medical products, in particular handpieces with similar degrees of contamination, are to be cleaned.

It is of particular advantage if a temperature sensor is integrated in the holding apparatus, which is configured to (continuously) detect a temperature curve or a temperature change or a temperature curve (over time) and to pass it on to the data processing device, and the data processing device is configured to drive a signal generator, which is configured to provide a user with indications or notifications or information or warnings, in particular via an optical and/or acoustic signal. Accordingly, at least one temperature sensor is preferably provided, which detects an amount and a duration of a temperature change or a temperature course over time.

The data processing device is preferably configured to detect a cleaning process or a cleaning oil process via the temperature course or a temperature change or the temperature curve (over time) or to draw conclusions as to whether a (performed) cleaning process or a (performed) cleaning oil process has been suitably carried out.

For example, a cleaning process is detected when the temperature measured by the temperature sensor exceeds a predetermined temperature indicative of a cleaning process. The predetermined temperature can, for example, be a temperature between 50° C. and 70° C. Particularly preferably, the predetermined temperature is about 60° C.

Preferably, the signal generator indicates to the user how long the cleaning process or the cleaning oil process has to be performed. Alternatively or additionally, after the (performed) cleaning process or after the (performed) cleaning oil process, the signal generator preferably indicates to the user whether the corresponding cleaning process or cleaning oil process has been suitably performed. Alternatively or additionally, the signal generator preferably indicates to the user which step the user has to perform next.

For example, after detecting the cleaning process or after performing the cleaning process, the data processing device can drive the signal generator, which is preferably an optical or acoustic signal generator, to inform the user, preferably by means of an optical or acoustic signal, whether the cleaning process has been suitably performed.

Furthermore, after detecting the cleaning process or after carrying out the cleaning process, the data processing device can drive the signal generator, which is preferably an optical or acoustic signal generator, so that it informs the user that the user has to carry out the next step of maintaining the medical product with cleaning oil (cleaning oil process). This is particularly important, since the absolutely necessary cleaning oil process of the medical products after the cleaning process in a washer-disinfector (WD) is often forgotten or not known by the cleaning personnel. For example, an optical warning message (e.g. red LED) and/or a suitable optical symbol can be displayed to the user, informing him/her that the next step to be taken has to be the maintenance of the medical product with cleaning oil.

The data processing device is preferably configured to also detect the cleaning oil process. In particular, after a start of the cleaning oil process, the temperature at the temperature sensor drops abruptly (approx. 20K or 20° C. in the first second) due to the expansion cooling of the propellant. Since the temperature sensor constantly/continuously records the temperature course, it also detects this abrupt drop in temperature within a very short time. The data processing device preferably detects whether the cleaning oil process has been carried out (yes/no), and whether the cleaning oil process has been carried out in a suitable manner (in particular via the shape/type of temperature drop and its duration). The signal generator can thus preferably also inform the user (by means of a visual or acoustic signal) whether the cleaning oil process has been suitably carried out. In addition, a suitable/required time of the cleaning oil process can preferably be determined via the shape of the temperature drop and its duration and can be communicated to the user (by an acoustic and/or optical signal, for example by an LED turning off).

A preferred configuration example is characterized in that two temperature sensors, namely a first temperature sensor and a second temperature sensor, are provided, wherein the first temperature sensor is provided in a supply line of the holding apparatus, and the second temperature sensor is provided outside the supply line on the holding apparatus and is provided for a reference measurement. Thus, in other words, two temperature sensors are particularly preferably provided.

In an advantageous implementation of the idea of the invention, it is provided that the data processing device is/can be connected to a data memory of the medical product, wherein the cleaning information is/can be stored in the data memory. Accordingly, it is provided that the data processing device writes the determined cleaning information into the data memory of the medical product. In the case of motors and/or handpieces which are connected to an associated control device prior to use, it is provided that the stored cleaning information can be read out and/or displayed by the control device. Such data transmission can be carried out, for example, via a wired connection or by radio.

In such an embodiment of the holding apparatus, the cleaning information is linked to an identity of the medical product by writing the cleaning information associated with the medical product directly into the data memory of the medical product.

In an advantageous embodiment of the holding apparatus, it is provided that the holding apparatus has at least one identification assembly which is/can be brought into operative connection with the data processing device and by means of which the medical product arranged in the holding apparatus can be identified on the basis of an identification feature, wherein by means of the data processing device the identification feature can be linked to the cleaning information to become product information of the medical product. Such an embodiment of the invention makes it possible that the cleaning information processed into product information can be transferred independently of the medical product and is thus also suitable for use in the context of an external analysis, in inventory monitoring, in monitoring service intervals or the like.

It is provided that the identification assembly can be, for example, a reader for reading an NFC chip, wherein the identification feature is an NFC chip arranged on the medical product. Identification feature in the sense of the invention denotes all means as well as identification information stored therein, which are suitable to identify an object by means of an automatable method. When the cleaning information is linked to the identification feature, the cleaning information is extended by the identification information of the identification feature. Identification features are in particular NFC chips, resistor codes, EEPROMs, bar codes, machine-readable number sequences or the like. It is also possible that the identification assembly is partially or fully integrated into the data processing device.

The identification assembly can be brought into operative connection with the data processing device both by means of a cable and wirelessly. It is provided that the wireless connection can be established, for example, by means of a radio standard, such as WLAN.

An advantageous embodiment of the invention provides that identification of the medical product is carried out at least in part by means of a wireless method. Identification of the medical product in the sense of the invention means in particular which combination of identification assembly and identification feature is used to identify the medical product. In this context, wireless methods include both radio-based, electronic methods and, for example, optical methods. Radio-based, electronic methods include, for example, the use of RFID technology, WLAN, NFC or the like. Optical methods include, for example, the use of QR codes, bar codes, machine-readable number sequences or the like.

It is also possible, and possibly provided according to the invention, that identification of the medical product is at least partially carried out by means of a cable-based method. For cable-based methods, it is provided that a physical connection, in particular a cable connection, is/is being established between the identification assembly and the identification feature. Identification features suitable in particular for cable-based identification are, for example, resistor codes, EEPROMs or the like.

It is also possible and, if necessary, provided that different identification means can be used in parallel in order to achieve redundancy in the identification of the medical product. In particular, this reduces the error rate in identifying the medical product and increases failure safety.

In order to achieve a direct transmission of the cleaning information and/or product information from the data processing device to the evaluation device, it is provided according to the invention, if necessary, that the data processing device has a transmission device and/or is/can be brought into operative connection with a transmission device in a data-conducting manner, wherein a data-conducting connection between the data processing device and the evaluation device is/can be established via the transmission device, by means of which cleaning information and/or product information can be transmitted from the data processing device to the evaluation device. Such a design of the holding apparatus according to the invention is in particular advantageous if the medical products to be cleaned do not have their own data memory. Such medical products are, for example, compressed-air handpieces, reprocessable implants, tools, instruments or the like. It is provided that the evaluation device may be, for example, a PC, a tablet, a smartphone or the like. It is particularly advantageous in this embodiment that, for example, the contents of a sterile container can be checked without having to open it and thus breaking its seal.

Further alternatively, it can be provided that the transmission device is configured in such a way that a data-conducting connection to the evaluation device can be established by means of a radio standard, in particular a mobile radio standard, a WLAN standard and/or a near-field communication standard. The use of a radio standard simplifies the connection of the evaluation device to the data processing device by means of the transmission device, since standardized protocols can be used. However, it is also possible to use a generic radio standard to establish the connection.

The invention also relates to a product monitoring system for monitoring medical products, which has at least one of the described holding apparatuses and at least one evaluation device according to the invention. It is also possible that the product monitoring system comprises a plurality of holding apparatuses which is/can be brought into operative connection with one or more evaluation devices. Such a product monitoring system makes it possible for a large number of medical products to be monitored without contact by means of the evaluation device. It is particularly advantageous compared to the prior art that medical products which can otherwise only be monitored as a set, such as reprocessable implants, can also be individually monitored.

It is provided that the product information between the holding apparatus and the evaluation device can be transmitted both directly and indirectly. A direct connection can be wireless or cable-based. It is provided that an indirect connection can be established in particular via the data memory of the medical product, namely in that the data memory is first connected to the holding apparatus and the product information is stored on the data memory and then the medical product together with the data memory is connected to the evaluation device so that the product information can be read out from the data memory by the evaluation device.

In order to enable assignment of the product information to the correct medical product by the evaluation device, it is provided that the evaluation device can have means for reading out information features or product information stored in the data memory of the medical product.

An advantageous embodiment of the invention provides that the evaluation device is/can be brought into operative connection with an external storage medium, wherein the cleaning information and/or product information can be transferred from the data processing device via the evaluation device to the external storage medium. Such a design of the product monitoring system enables cleaning information to be exported and evaluated and/or stored on external systems. This facilitates measures for quality assurance and hygienic monitoring with regard to the medical products.

In an advantageous embodiment of the product monitoring system according to the invention, it is provided that the external storage medium is a cloud storage. By storing the cleaning information in a cloud storage, it is made possible that a responsible group of persons, in particular surgeons, personnel of the central sterile supply department, the manufacturer and the like, can receive information about a condition of the medical products independent of location.

In addition, the manufacturer of the medical products is enabled to carry out and/or coordinate product updates, recalls or similar actions in a centralized manner and with reduced organizational effort.

BRIEF DESCRIPTION OF THE DRAWING FIGURES

The invention is explained in more detail below by way of preferred configuration examples with reference to the accompanying figures.

DETAILED DESCRIPTION

Figure 1:
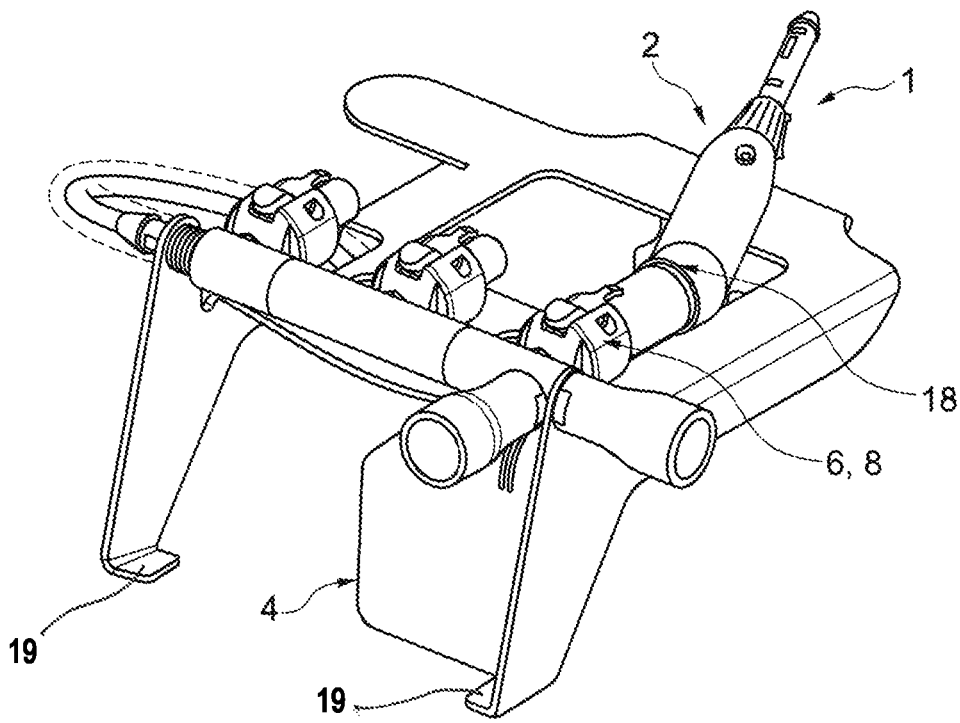
FIG. 1 shows an isometric view of an embodiment of the holding apparatus.
Figure 2:
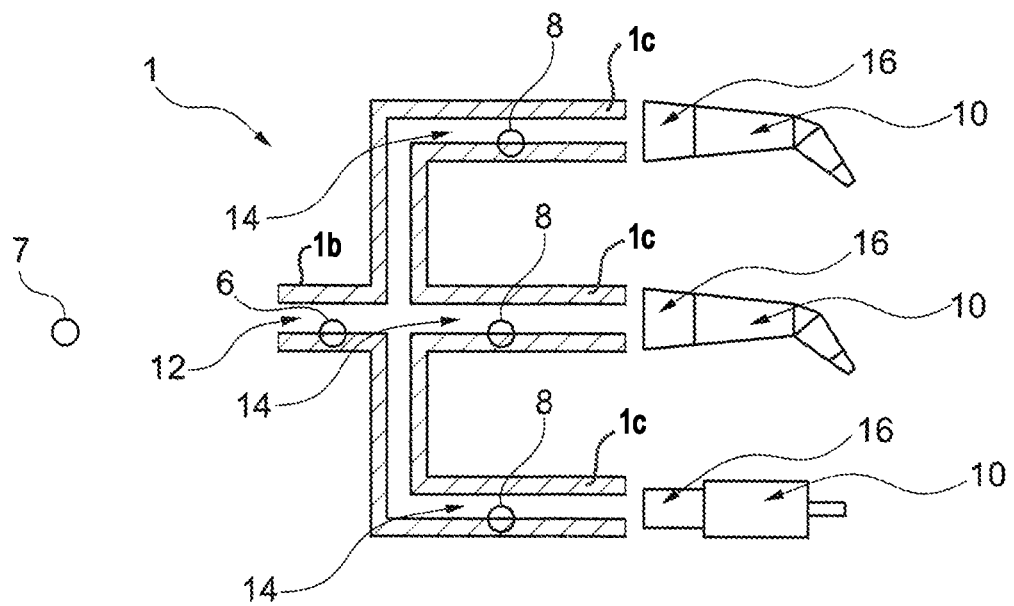
FIG. 2 shows a schematically represented and simplified sectional view of the holding apparatus shown in FIG. 1.
Figure 3:
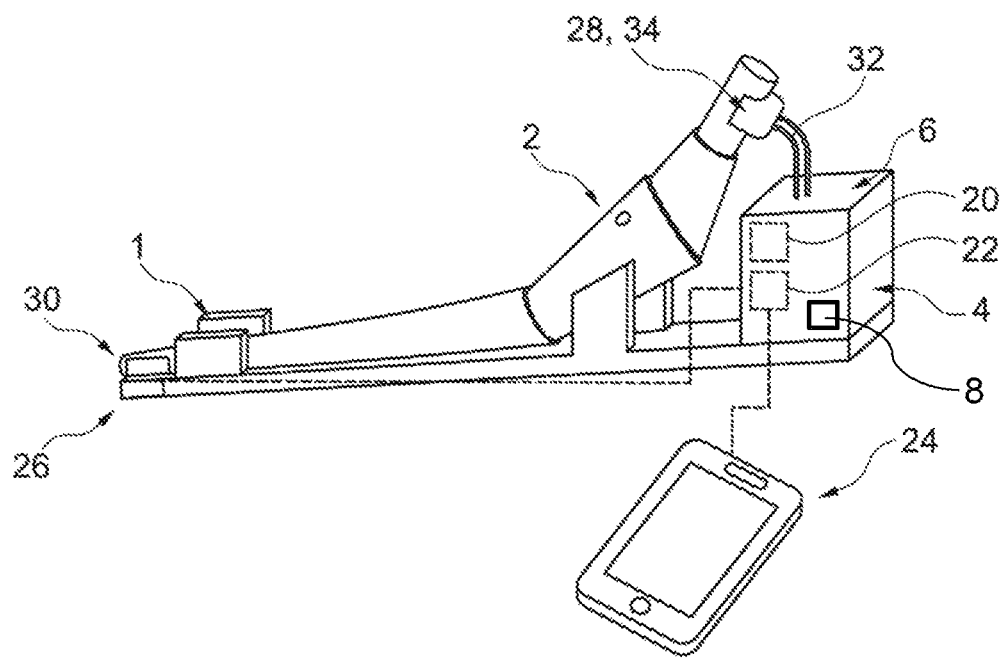
FIG. 3 shows a schematically represented side view of an embodiment of the holding apparatus.

FIGS. 1 to 3 each show an embodiment of a holding apparatus 1 for holding at least one sterilizable medical product 2 during a cleaning process and for storing the medical product 2 before and after the cleaning process. The medical product 2 is arranged in the holding apparatus 1 and is held by it in such a way that it can change its position neither during the cleaning process, nor during transport. The holding apparatuses 1 shown are configured in such a way that they can be arranged inside a sterile container, which is not shown, if required.

For this purpose, the holding apparatus 1 consists of a platform-like (grid) frame, for example a sheet metal frame, with supporting feet 19, to which at least one pipeline 1b is fixed, which has a number of branches 1c along the pipeline 1b, which form connection points/connection nozzles for the hollow medical products 2 such as handpieces. In the area of these connection points, the (sheet metal) frame defines in each case a recess/depression or clamping jaws for stable mounting of the respective medical product.

The holding apparatus 1 shown comprises a respective data processing device 4 as well as at least one temperature sensor 6 for detecting a temperature, which can be arranged, for example, in the region of the connection points 1c. The holding apparatus 1 shown in FIGS. 1 and 2 furthermore also has at least one pressure sensor 8 for detecting a static pressure of a cleaning liquid, which is likewise arranged in the region of the connection point 1c.

The sectional view shown in FIG. 2 of the holding apparatus 1 shown in FIG. 1 shows the internal structure of the holding apparatus 1, which is adapted in particular to the cleaning of handpieces 10. The holding apparatus 1 has a supply line 12 and three cleaning lines 14 branching off from the supply line 12, which form the aforementioned connection points 1c. A respective rinsing receptacle 16 for (fluidically) receiving/connecting a handpiece 10 is connected/formed to each of the cleaning lines 14. The cleaning agent can be supplied to the handpieces 10 through the supply line 12, the cleaning lines 14 and the rinsing receptacle 16. A respective pressure sensor 8 is arranged in each of the cleaning lines 14 and a temperature sensor 6 is arranged in the supply line 12. In addition to the temperature sensor 6, a second temperature sensor 7 can be attached to the holding apparatus 1 outside the supply line 12, which serves for taking a reference measurement. The data-conducting connection between the sensors 6, 8 and the data processing device 4 is not shown in FIG. 2.

The data processing device 4 is connected to the sensors 6, 8 in a signal-conducting manner and processes the sensor signals into cleaning information.

The provided temperature sensor 6 continuously detects a temperature course and passes it on to the data processing device 4. For example, the data processing device 4 recognizes that a cleaning process is being carried out in a washer-disinfector when the temperature exceeds a predetermined value, which is approximately 60° C. The data processing device 4 further detects whether the cleaning process has been performed in a suitable manner, and may drive a signal generator 8, such as an LED 8, so that the signal generator indicates (acoustically or visually) to a user that the cleaning process has been performed in an appropriate manner.

Furthermore, the data processing device 4 can control the signal generator 8 so that the signal generator informs the user that in a next step (after the cleaning process in the washer-disinfector) the medical product has to be maintained with cleaning oil (cleaning oil process), in particular since this step is often forgotten or not known by cleaning staff.

After a start of the cleaning oil process, the temperature at the temperature sensor 6 drops abruptly (about 20K/20° C. in the first second) due to expansion cooling of the propellant. This temperature drop is detected by the temperature sensor 6 and is recognized by the data processing device 4. Thus, the data processing device 4 also detects whether the cleaning oil process is being performed. Via a shape and a duration of the temperature drop, the data processing device 4 furthermore also recognizes whether the cleaning oil process has been suitably carried out, or the data processing device 4 can inform the user via the signal generator 8 of a suitable/required time of the cleaning oil process.

The data processing device 4 of the holding apparatus 1 shown in FIG. 1 is connected to a data memory 18 of the (in the) medical product 2, on which the cleaning information is stored. In contrast, the holding apparatus 1 shown in FIG. 3 has an internal storage device 20 (as an alternative to the external data memory 18).

The data processing device 4 of the holding apparatus 1 shown in FIG. 3 has a transmission device 22. The transmission device 22 is connected in a data-conducting manner by means of a radio standard to an evaluation device 24 (preferably) in the form of a smartphone. Furthermore, the holding apparatus 1 also has a first identification assembly 26 and a second identification assembly 28, both of which are connected to the data processing device 4. The first identification assembly 26 is adapted to a first identification feature 30 of the medical product 2, for example an effector tool shaft, and preferably identifies it wirelessly. The connection of the first identification assembly 26 to the data processing device 4 is also preferably designed as a wireless connection. The second identification assembly 28 is preferably connected to the data processing device 4 by means of a wire connection 32. It is further contacted with a second identification feature 34 of the medical product 2, for example, a connection section of the medical product. By means of the identification assemblies 26, 28, an identity of the medical product 2 can be determined based on identification information stored in the identification features 30, 34. By means of the data processing device 4, the identification information of the identification features 30, 34 (probe, scanner, etc.) is linked with the cleaning information to become product information of the medical product 2.

Via the data-conducting connection between the evaluation device 24 and the data processing device 4, both the currently available product information and the product information present in the storage device 20 are transmitted to the evaluation device 24.

Figure 4:
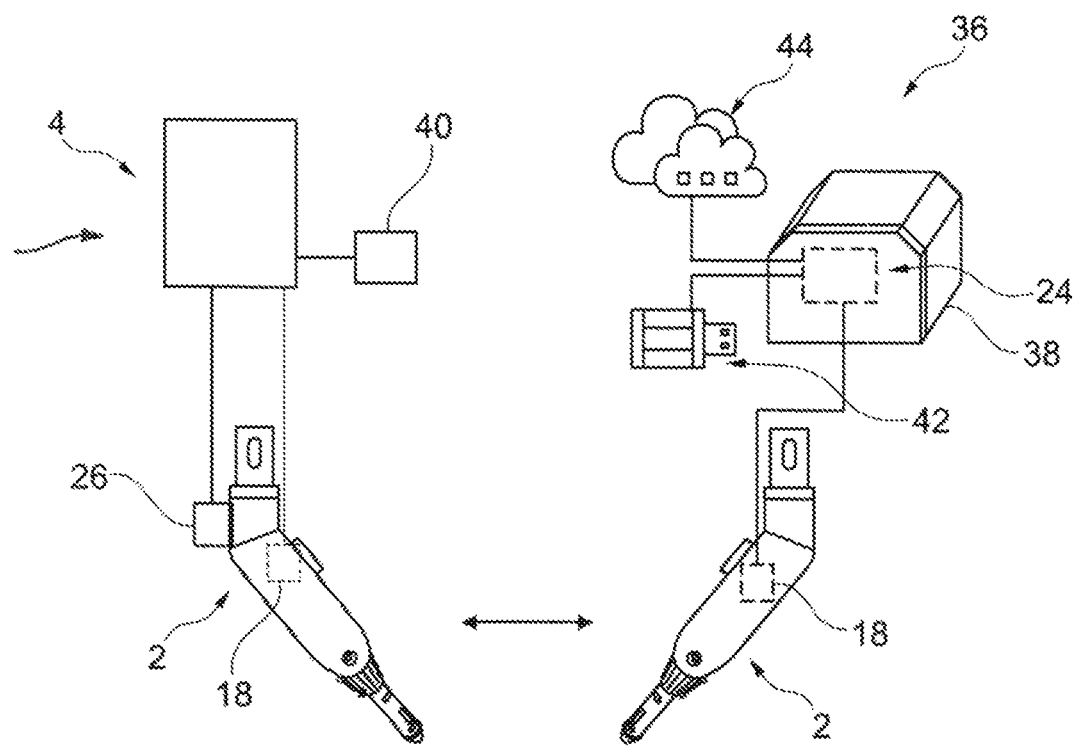
FIGS. 4 and 5 show schematic representations of embodiments of the product monitoring system.
Figure 5:
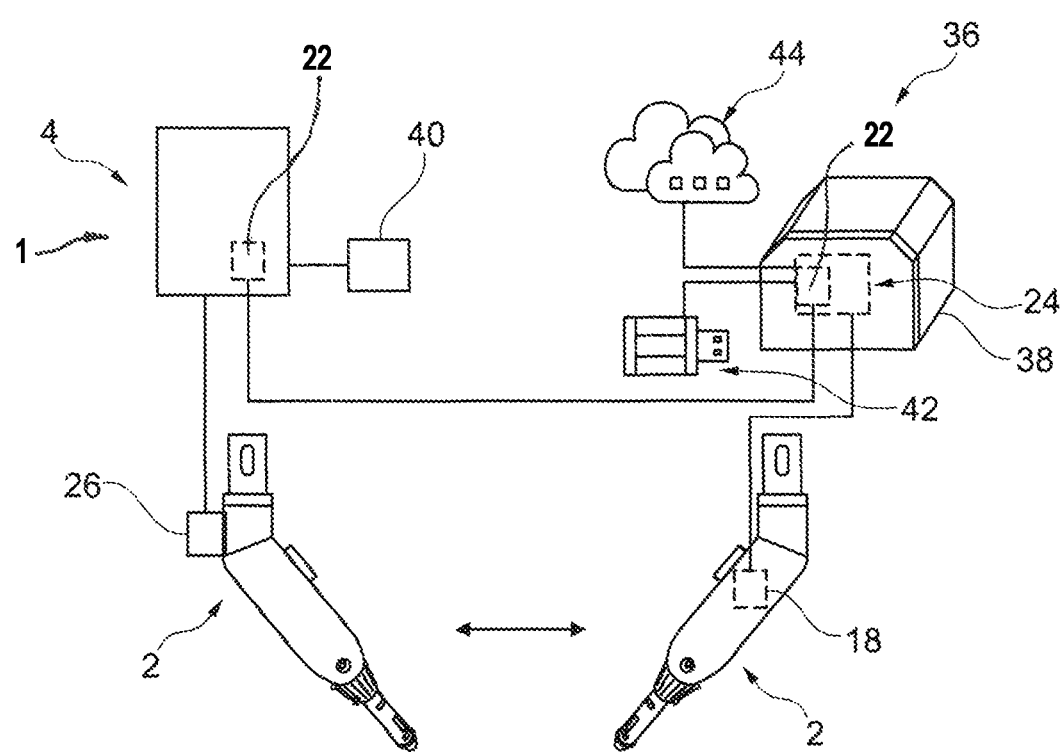

FIGS. 4 and 5 each show schematically illustrated embodiments of a product monitoring system 36 comprising a (separate) evaluation device 24 and a holding device 1 with a data processing device 4. The evaluation device 24 is integrated, for example, into a control device 38 for controlling a motor-driven medical product 2, in which the data memory 18 is accommodated. The holding apparatus 1 has an energy storage device 40 which supplies the data processing device 4 arranged thereon with electrical energy and thus enables its autonomous operation. In addition, the holding apparatus 1 of the illustrated product monitoring system 36 has a respective first identification assembly 26, so that medical products 2 can be identified with identification features. In the embodiments shown according to FIGS. 4 and 5, the evaluation device 24 is preferably connected to a USB stick 42 and to a cloud storage 44. The product information can thus be transferred from the data processing device 4 of the holding apparatus 1 via the (external) evaluation device 24 both to the USB stick 42 and to the cloud storage 44.

In the product monitoring system 36 shown in FIG. 4, the data processing device 4 does not have an additional transmission device 22. In this case, the connection between the data processing device 4 and the evaluation device 24 is indirect, by means of the data memory 18 of the medical product 2. In contrast, in the product monitoring system 36 shown in FIG. 5, both the data processing device 4 and the evaluation device 24 have a transmission device 22, so that in the embodiment shown, a direct connection is also established between the data processing device 4 and the evaluation device 24. The medical product 2 is identified on the basis of data stored in the data memory 18, so that the product information can be assigned to the currently connected medical product 2 by the evaluation device 24.

The invention claimed is:

1. A holding apparatus for use inside an area to be cleaned and inside an area to be sterilized, and for holding at least one sterilizable medical product during a cleaning process and during a cleaning oil process, as well as for storing the medical product before and after the cleaning process and the cleaning oil process, wherein:
the holding apparatus has a data processing device connected to at least one temperature sensor configured to measure a temperature during the cleaning process and the cleaning oil process in a signal-conducting manner, wherein the at least one temperature sensor is arranged at the holding apparatus and is configured to detect and forward a temperature course or a temperature curve to the data processing device;
the data processing device has a storage device on which cleaning information is storable;
the cleaning information is retrievable or readable from the storage device by an evaluation device operable to determine a cleaning profile of the medical product based on the cleaning information;
the data processing device is configured to detect both the cleaning process and the cleaning oil process via the temperature course or the temperature curve, wherein the data processing device is configured to detect that the cleaning oil process is being performed based on an abrupt drop in the temperature detected by the at least one temperature sensor, and wherein the data processing device is configured to draw conclusions as to whether the cleaning oil process has been suitably carried out;
the holding apparatus further comprises a signal generator configured to output an acoustical or visual signal; and
the data processing device is configured to drive the signal generator to generate:
a first acoustical or visual signal indicating to a user that the cleaning process is completed;
a second acoustical or visual signal after the first acoustical or visual signal reminding the user that the cleaning oil process needs to be completed; and
a third acoustical or visual signal after the second acoustical or visual signal indicating to the user that the cleaning oil process is completed.

2. The holding apparatus according to claim 1, wherein the holding apparatus has a supply line and a plurality of cleaning lines that branch off from the supply line, each cleaning line being connected to a rinsing receptacle for receiving a handpiece, wherein a cleaning agent is suppliable through the supply line, each cleaning line and each rinsing receptacle to sections of handpieces to be cleaned.

3. The holding apparatus according to claim 2, wherein the at least one temperature sensor is arranged in the supply line and/or in one of the plurality of cleaning lines, and/or in the one of the rinsing receptacles.

4. The holding apparatus according to claim 1, wherein the signal generator indicates to the user how long the cleaning oil process has to be performed, and/or after the cleaning oil process has been performed, indicates to the user whether the cleaning oil process has been performed suitably and/or indicates to the user which step the user has to perform next.

5. The holding apparatus according to claim 1, wherein the at least one temperature sensor comprises a first temperature sensor and a second temperature sensor, and wherein the first temperature sensor is provided in a supply line of the holding apparatus, and the second temperature sensor is provided outside the supply line on the holding apparatus and is provided for a reference measurement.

6. The holding apparatus according to claim 1, wherein the data processing device is connectable to a data memory of the medical product, and wherein the cleaning information is storable in the data memory.

7. The holding apparatus according to claim 1, wherein the holding apparatus has at least one identification assembly configured for operative connection with the data processing device and by which the medical product arranged in the holding apparatus is identifiable based on an identification feature, wherein the identification feature is linkable with the cleaning information by the data processing device to become product information of the medical product.

8. The holding apparatus according to claim 1, wherein the data processing device has a transmission device, and wherein a data-conducting connection between the data processing device and the evaluation device is established via the transmission device, by which cleaning information and/or product information is transmittable from the data processing device to the evaluation device.

9. A product monitoring system for monitoring medical products with at least one holding apparatus according to claim 1 and at least one evaluation device.

10. The holding apparatus according to claim 1, wherein the holding apparatus further comprises a pressure sensor for determining a static and/or dynamic pressure of a cleaning agent.

11. The holding apparatus according to claim 1, wherein the abrupt drop in the temperature comprises a drop of 20° C. in one second due to expansion cooling of a propellant.

12. A holding apparatus for use inside an area to be cleaned and inside an area to be sterilized, and for holding at least one sterilizable medical product during a cleaning process and a cleaning oil process, as well as for storing the medical product before and after the cleaning process and the cleaning oil process, the holding apparatus comprising:
- a platform frame made of sheet metal with supporting feet;
- a data processing device;
- a storage device on which cleaning information is storable;
- an evaluation device operable to retrieve and read cleaning information from the storage device and determine a cleaning profile of the medical product based on the cleaning information;
- a supply line for connection to a supply of a cleaning agent;
- a plurality of cleaning lines which branch off from the supply line;
- a plurality of rinsing receptacles, each rinsing receptacle configured to attach to a handpiece to be cleaned;
- at least one temperature sensor arranged in the supply line and/or in one of the plurality of cleaning lines and/or in one of the rinsing receptacles, the at least one temperature sensor connected to the data processing device and configured to measure a temperature during the cleaning process and the cleaning oil process in a signal-conducting manner; and
- a signal generator configured to output an acoustical or visual signal,
wherein each cleaning line is connected to one of the plurality of rinsing receptacles,
wherein the cleaning agent is suppliable through the supply line, the plurality of cleaning lines and the rinsing receptacles to sections of handpieces to be cleaned, and
wherein the data processing device is configured to drive the signal generator to generate:
- a first acoustical or visual signal indicating that the cleaning process is completed;
- a second acoustical or visual signal after the first acoustical or visual signal reminding the user that the cleaning oil process needs to be completed; and
- a third acoustical or visual signal after the second acoustical or visual signal indicating to the user that the cleaning oil process is completed.

13. The holding apparatus according to claim 12, wherein:
the at least one temperature sensor is configured to detect a temperature course or a temperature curve and to forward the temperature course or the temperature curve to the data processing device,
the data processing device is configured to detect both the cleaning process and aand the cleaning oil process via the temperature course or the temperature curve,
the data processing device is configured to detect that the cleaning oil process is being performed based on an abrupt drop in temperature detected by the at least one temperature sensor, and
wherein the data processing device is configured to draw conclusions as to whether the cleaning oil process has been suitably carried out.

14. A holding apparatus for holding, storing, and transporting a medical product during and after a cleaning process and a cleaning oil process, the holding apparatus comprising:
- a platform defining a mounting recess for mounting the medical product on the platform during the cleaning process, the cleaning oil process, and during transport;
- a data processing device connected to the platform and comprising a storage device on which cleaning information for the medical product is storable;
- at least one temperature sensor connected to the data processing device, the at least one temperature sensor configured to measure a temperature during the cleaning process and the cleaning oil process; and
- a signal generator operatively connected to the data processing device and configured to output an acoustical or visual signal,
the data processing device configured to drive the signal generator to generate:
- a first acoustical or visual signal indicating to a user that the cleaning process is completed;
- a second acoustical or visual signal after the first acoustical or visual signal reminding the user that the cleaning oil process needs to be completed; and
- a third acoustical or visual signal after the second acoustical or visual signal indicating to the user that the cleaning oil process is completed.

15. The holding apparatus according to claim 14, wherein the mounting recess is configured to fix the position of the medical product relative to the platform during the cleaning process, the cleaning oil process, and during storage and transport.

16. The holding apparatus according to claim 14, wherein the mounting recess comprises a first mounting recess for mounting a first section of the medical product and a second mounting recess for mounting a second section of the medical product.

17. The holding apparatus according to claim 16, wherein the first mounting recess comprises a first identification assembly connected to the data processing device, and the second mounting recess comprises a second identification assembly connected to the data processing device.

18. The holding apparatus according to claim 17, wherein the first identification assembly is configured to identify a first identification feature on the first section of the medical product, and the second identification assembly is configured to identify a second identification feature on the second section of the medical product.

19. The holding apparatus according to claim 14, further comprising a supply line for connection to a source of cleaning agent and at least one cleaning line that branches off of the supply line.

20. The holding apparatus according to claim 19, wherein the at least one cleaning line comprises a connection point configured to fluidly connect to the medical product when the medical product is mounted in the mounting recess.

21. The holding apparatus according to claim 20, wherein the at least one cleaning line comprises a plurality of cleaning lines that branch off of the supply line, and wherein the connection points on the plurality of cleaning lines are arranged in series on the platform.

22. The holding apparatus according to claim 14, wherein the platform is configured to elevate at least a portion of the medical product above a surface on which the platform is supported.

23. The holding apparatus according to claim 22, wherein the platform comprises a frame configured for mounting in a sterilization container.

24. The holding apparatus according to claim 23, wherein the frame comprises a supporting foot that elevates the recess above the support surface.

* * * * *